(12) United States Patent
Leroux et al.

(10) Patent No.: US 9,289,251 B2
(45) Date of Patent: *Mar. 22, 2016

(54) SURGICAL DEVICE FOR CORRECTING DEFORMATIONS IN THE SPINAL COLUMN

(75) Inventors: Stéphane Leroux, Lyons (FR); Philippe Laurito, Le Val (FR); José Ignacio Maruenda Paulino, Valencia (ES)

(73) Assignee: SPINEWAY, Ecully (FR)

( * ) Notice: Subject to any disclaimer, the term of this patent is extended or adjusted under 35 U.S.C. 154(b) by 199 days.

This patent is subject to a terminal disclaimer.

(21) Appl. No.: 14/128,814

(22) PCT Filed: Jun. 20, 2012
(Under 37 CFR 1.47)

(86) PCT No.: PCT/FR2012/051392
§ 371 (c)(1),
(2), (4) Date: May 5, 2014

(87) PCT Pub. No.: WO2012/175871
PCT Pub. Date: Dec. 27, 2012

(65) Prior Publication Data
US 2014/0350612 A1    Nov. 27, 2014

(30) Foreign Application Priority Data

Jun. 23, 2011 (FR) ...................................... 11 55563

(51) Int. Cl.
*A61B 17/70* (2006.01)

(52) U.S. Cl.
CPC ........... *A61B 17/7085* (2013.01); *A61B 17/708* (2013.01); *A61B 17/7079* (2013.01)

(58) Field of Classification Search
USPC ........................................................ 606/86 A
See application file for complete search history.

(56) References Cited

U.S. PATENT DOCUMENTS

| 8,500,741 B2 * | 8/2013 | Hansen .............. | A61B 17/7074 606/103 |
| 2006/0036255 A1 * | 2/2006 | Pond, Jr. ............ | A61B 17/7079 606/86 R |

(Continued)

FOREIGN PATENT DOCUMENTS

FR          1151331 A          1/1958

OTHER PUBLICATIONS

International Search Report for International Application No. PCT/FR2012/051392, dated Aug. 31, 2012.

*Primary Examiner* — Jan Christopher Merene
(74) *Attorney, Agent, or Firm* — Heslin Rothenberg Farley & Mesiti P.C.

(57) ABSTRACT

The device includes tubular elements capable of being temporarily fastened at the level of pedicle screw heads arranged to be connected by an implantable curved rod, and at least one rod intended to be movably inserted into slots of each tubular element, to align them for the correction of the spinal column by translation, tilting, and rotation of the vertebrae in the three planes of space. Each tubular element is configured in such a way that it can be coupled with the outside of the pedicle screw heads. The rod forms an alignment and handling rod, being capable of acting, as it moves, on rings for simultaneously displacing the curved rod. Each ring is assembled with the ability to slide along the tubular element, and to be height-adjustable to compensate for dimensional deviations between the alignment and handling rod and the curved rod.

9 Claims, 12 Drawing Sheets

(56) References Cited

U.S. PATENT DOCUMENTS

| | | | |
|---|---|---|---|
| 2006/0271050 A1 | 11/2006 | Piza Vallespir | |
| 2007/0093824 A1* | 4/2007 | Hestad | A61B 17/7032 606/261 |
| 2007/0233079 A1 | 10/2007 | Fallin et al. | |
| 2008/0125817 A1* | 5/2008 | Arnett | A61B 17/7002 606/319 |
| 2008/0262551 A1* | 10/2008 | Rice | A61B 17/8869 606/268 |
| 2009/0228053 A1* | 9/2009 | Kolb | A61B 17/7076 606/86 A |
| 2010/0114179 A1 | 5/2010 | Moore | |
| 2012/0271365 A1* | 10/2012 | Daubs | A61B 17/7086 606/86 A |
| 2014/0163625 A1* | 6/2014 | Meyer | A61B 17/7091 606/86 A |
| 2015/0127053 A1* | 5/2015 | Maruenda Paulino | A61B 17/708 606/267 |

* cited by examiner

SURGICAL DEVICE FOR CORRECTING DEFORMATIONS IN THE SPINAL COLUMN

CROSS REFERENCE TO RELATED APPLICATIONS

This application is a national stage filing under section 371 of International Application No. PCT/FR2012/051392, filed on Jun. 20, 2012, and published in French on Dec. 27, 2012, as WO 2012/175871 and claims priority of French application No. 1155563 filed on Jun. 23, 2011, the entire disclosure of these applications being hereby incorporated herein by reference.

BACKGROUND ART

The invention relates to the technical field of surgical instruments for correcting a deformation of the spinal column.

The invention is particularly advantageously for scoliosis correction.

The invention more specifically relates to the basic principle of a correction such as defined in patent application FR1151331 of the applicant.

This patent application mainly relates to a surgical device for correcting a deformation of the spinal column. This device comprises tubular elements capable of being temporarily attached at the level of pedicle screw heads arranged to be connected by an implantable curved rod. At least one rod is intended to be movably inserted into slots of each tubular element to align them in order to correct said column, by translation, tilting, and rotation of the vertebrae, in the three planes of space generally over several vertebrae and directly by acting on the rod inserted into said tubular elements. Each tubular element is designed in such a way that it can be coupled to the outside of the pedicle screw heads. The rod, which is an alignment and handling rod, is capable of acting, as it displaces, on means for simultaneously displacing the curved rod, previously inserted into the slots, towards the pedicle screw heads. Another rod is intended to be coupled to the outside of the aligned tubular elements to enable to remove the alignment and handling rod in order to enable the insertion, into each tubular element, of a member for actuating a nut for fastening the curved rod in each of the pedicle screw heads.

BRIEF SUMMARY OF INVENTION

Importantly, in this surgical device, each tubular element is made of two independent parts, one of the ends of each portion having fittings for coupling, on the one hand, said parts together and, on the other hand, of the parts with the corresponding pedicle screw head.

Based on this basic solution, a problem that the invention aims at solving is to improve the operation technique by facilitating the surgeon's task with, further, the possibility of intervening on both sides of the column (the convex side and the concave side), still with the aim of ensuring the double function of, on the one hand, rectifying the spinal bodies by means of tubular elements and, on the other hand, positioning the implantable rod and fastening it at the level of the pedicle screw heads, without having to take apart said tubular elements.

Another problem that the invention aims at solving is to adapt to the final lordosiskyphosis profile desired by the doctor to distribute the distraction stress to install the implantable curved rod, simultaneously on many vertebrae.

To solve such a problem, the implantable curved rod displacement means are formed of a ring mounted in such a way that it can slide along the tubular element, said ring being fitted to be height-adjustable so as to compensate for dimensional deviations between the rectilinear alignment and handling rod and the curved rod.

As a result, the alignment and handling rod, in combination with the height-adjustable rings, enables to exert a pressure force on almost the entire surface of the curved rod.

Another problem that the present invention aims at solving is to ease the lowering of rods into the tube slots by significantly decreasing the stress which should be exerted on said rods. To solve such a problem, the end of each tubular element, from which the actuation member is engaged, has a tapped socket for the screwing of a pusher member arranged to exert a pressure force on the alignment and handling rod to simultaneously cause the downward motion of the height-adjustable rings and of the implantable curved rod.

To solve the problem of exerting the pressure force, the pusher member has a threaded rod capable of being screwed into the tapped socket, one of the ends of said rod being fitted with a control handle while its other end is fitted with a rotatably-assembled tip and having a recess with a section complementary to that of the alignment and handling rod.

To solve the problem of coupling to the outside of the tubular elements the other rod, after having removed the alignment and handling rod in order to clear the passage inside of the tubular elements, the end of each tubular element has, opposite to its coupling with the pedicle screw head, an added collar with a laterally-protruding portion for the other rod to engage into it.

Each collar may be arranged at a different height along the tubular elements or the caps. The advantage is to be able to adapt the position of the instruments, particularly of the spacer members, to the patient's morphology to improve the corrections of the position of the vertebrae.

To solve the problem of coupling the tubular elements outside of the screw head with the aim of totally clearing the inside of said heads, each tubular element is made of two independent parts, one of the ends of each part having fittings for coupling said parts together and with respect to the corresponding pedicle screw head.

The coupling fittings are formed of two forks capable of being connected in jointed fashion, to enable to space apart the parts to position them with respect to the pedicle screw head, and then to push them back in order to clamp said head maintained between said parts by holding means.

To solve the problem of forming the tubular element as such for the insertion of the different rods, the other end of each part forming said element cooperates, after having been pushed back, with a hollow connection nut, said parts delimiting the diametrically-opposite slots for the rod insertion.

BRIEF DESCRIPTION OF THE DRAWING FIGURES

The invention is discussed hereafter in further detail by means of the accompanying drawings, among which:

DETAILED DESCRIPTION

Figure 1:
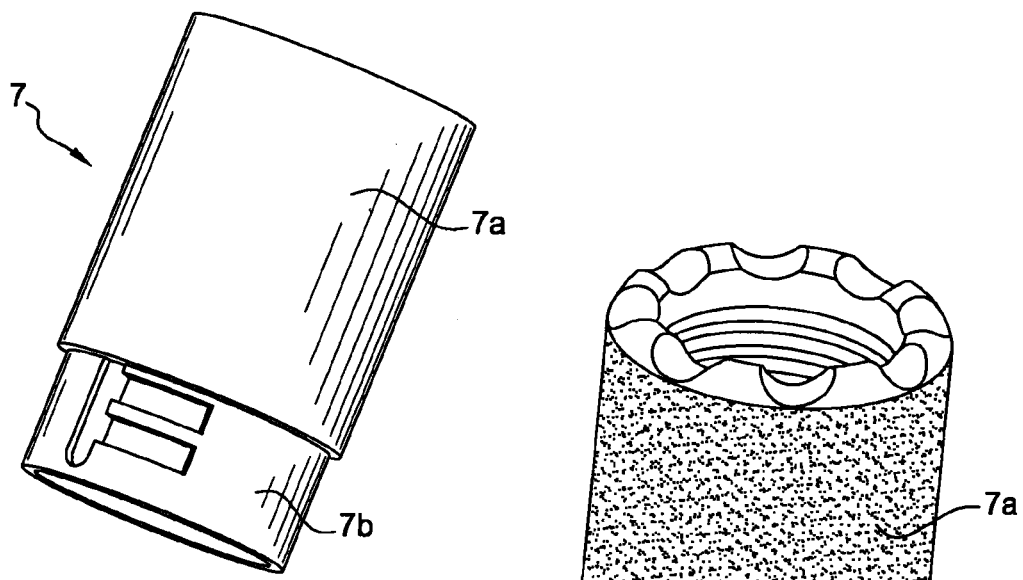
FIGS. 1 and 2 are perspective views of embodiments of a height-adjustable ring.

The surgical device according to the invention provides technical improvements to the device described in above-mentioned patent application FR 1151331.

In this respect, it should be reminded, for a better understanding of the following description, that the surgical device comprises tubular elements (1) capable of being temporarily attached at the level of pedicle screw heads (2) arranged to be connected by a distraction or compression implantable curved rod (3), to perform the correction directly and generally simultaneously on several vertebrae, for example, ten. A rod (4) is intended to be engaged through slots (1*c*) and (1*d*) of the different tubular elements (1). Rod (4) thus forms an alignment and handling rod for aligning the tubular elements (1), to provide the spinal column correction after a rotation, a translation, and a tilting, in the three planes of space, of a plurality of vertebrae (V), resulting from said alignment.

The aim is to be able to align the different tubular elements (1), resulting in the straightening up of the different vertebrae (V), and then, within the same operating time, with no disassembly, installing the implantable curved correction rod (3) in the different screw heads (2) to fix the obtained correction. It should be noted that there is no loss of the obtained correction, the insertion of the curved rod occurring at the center of the tubular guiding elements, once the correction is obtained.

Each tubular element (1) designed in such a way that it can be coupled to the outside of the pedicle screw heads (2).

It should be noted that the shape of the lower part of each tubular element has a very large surface area of contact with the external surfaces of the screw head, which reinforces the attachment rigidity and the cohesion of the tubular elements and the screws, to displace, correct, and control the displacement of the position of the vertebrae to rectify the deformation.

Each tubular element (1) is made of two independent parts (1*a*) and (1*b*). One of the ends of each part (1*a*) and (1*b*) has fittings provided to ensure the coupling, on the one hand, of the parts together and, on the other hand, with respect to the corresponding pedicle screw head (2). Such coupling fittings are for example formed by two forks capable of being connected in jointed fashion. For example, the branches of one of the forks have inner studs behaving as axes cooperating with recesses of the external surface of the branches of the other fork.

The coupling of the two parts (1*a*) and (1*b*), which thus are semi-tubular elements, is performed circularly at the contact with the external surface of the pedicle screw heads (2).

This enables to space apart parts (1*a*) and (1*b*) to position them relative to pedicle screw head (2), and then to push them back to clamp said pedicle screw head. It should be noted that pedicle screw head (2) has holding fittings cooperating with complementary fittings of at least one of the other parts (1*a*) and (1*b*). For example, such fittings are formed by at least one lug or other indexing means of one of parts (1*a*) and (1*b*) close to corresponding fork and capable of cooperating with a blind hole of a portion of the pedicle screw head (2).

After coupling of parts (1*a*) and (1*b*), as indicated, the latter delimit diametrically opposite slots (1*c*) and (1*d*).

Alignment rod (4) is inserted into slots (1*c*) and (1*d*) in such a way that it can move perpendicularly to the axis of the tubular elements (1).

The other end of each part (1*a*) and (1*b*) cooperates, after having been pushed back, as indicated previously, with a hollow cap (6) capable of ensuring the connection of said parts to form the tubular element as such.

As will be indicated in the following description, the rod (4) is capable of acting, as it moves, on means (7) for simultaneously displacing the implantable curved rod (3) previously inserted into slots (1*c*) and (1*d*).

It should be reminded that these different characteristics mostly follow from the teachings of document FR 1151331.

According to the present invention, the means (7) for displacing the implantable curved rod (3) are formed of a ring assembled in such a way that it can slide along the tubular element. The ring (7) is fitted to be height-adjustable so as to compensate for dimensional deviations between the rectilinear alignment and handling rod (4) and the curved rod (3). Advantageously, each ring (7) is made of two parts (7*a*) and (7*b*) coupled together in height-adjustable fashion.

Figure 2:
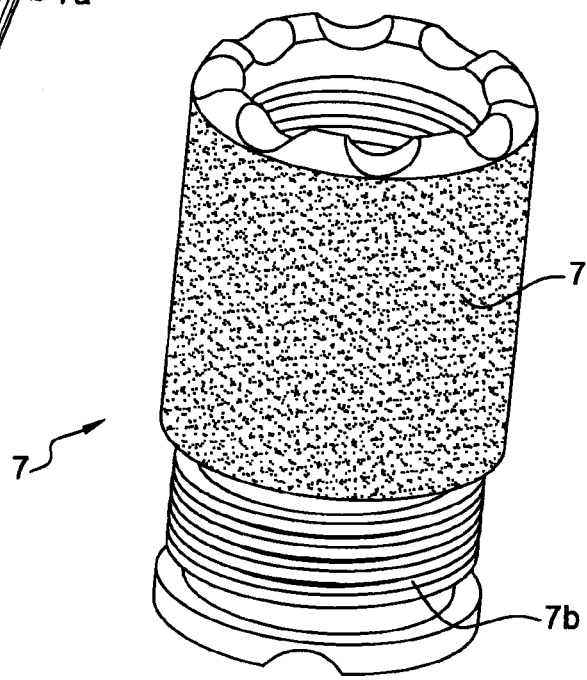
Figure 3:
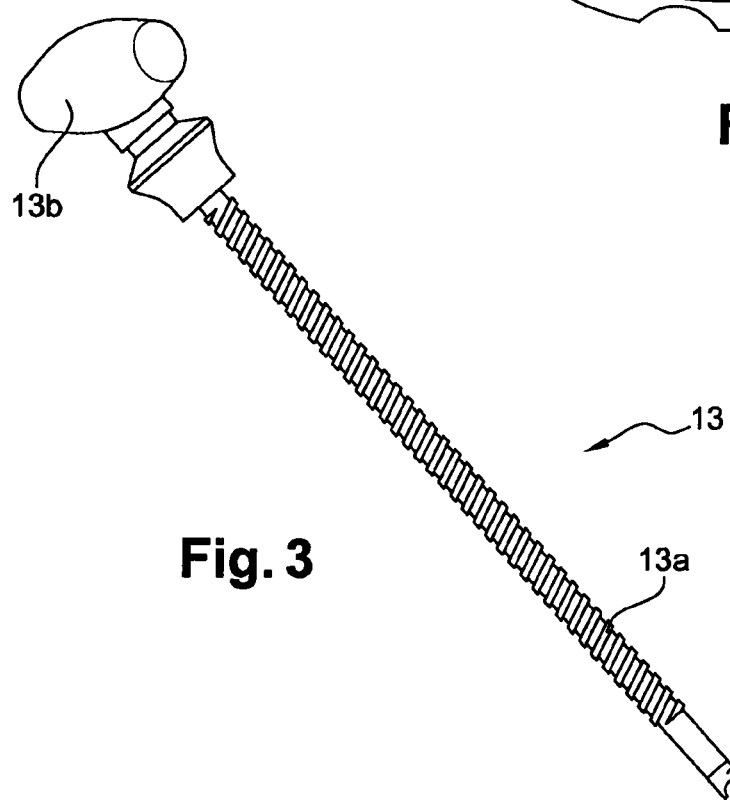
FIG. 3 is a perspective view of the pusher member.
Figure 4:
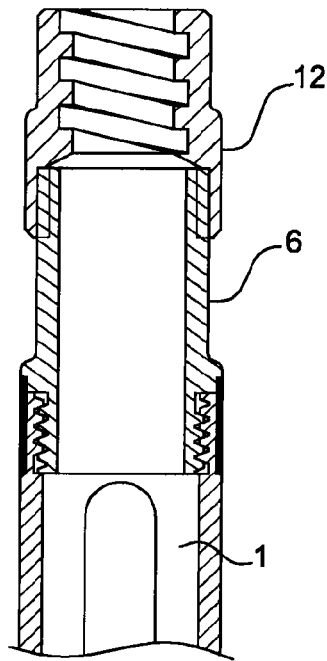
FIG. 4 is a partial cross-section view of the upper end of a tube equipped with a tapped socket for the screwing of the body of the pusher member.
Figure 5:
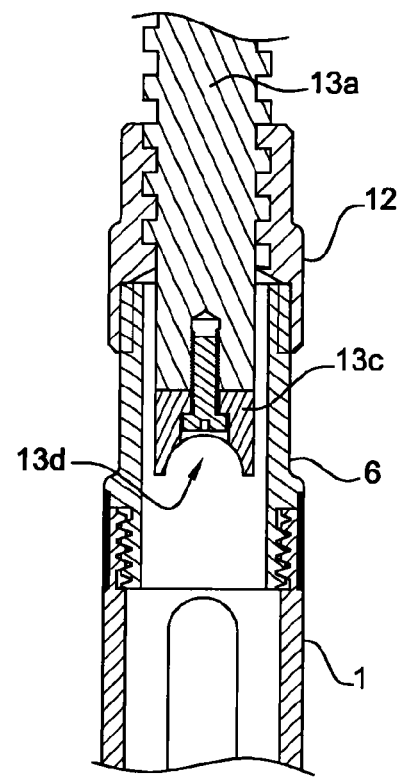
FIG. 5 is a view corresponding to FIG. 4 showing the engagement of the end of the extractor body.
Figure 6:
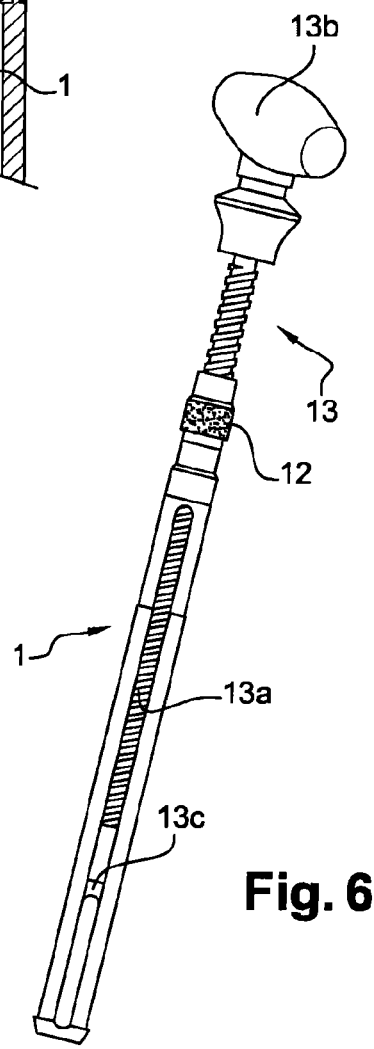
FIG. 6 is a perspective view showing the installation of the pusher member in a tubular element.

In the embodiment illustrated in FIG. 2, the two parts (7*a*) and (7*b*) are coupled by a specific threading system or parts (7*a*) and (7*b*) are assembled with the ability of being angularly indexed to the desired position (FIG. 1). The ring (7) may have, at its base, diametrically opposite recesses capable of being positioned in front of slots (1*c*) and (1*d*) to cooperate with the section of the curved rod (3). This ensures the indexing of the curved rod, avoiding its rotating on itself as it moves, as will be indicated in the following description. The height adjustment of the rings (7) enables to distribute the stress all along the rod (3). It should be noted that at the beginning of the intervention, rings (7) are at a minimum height enabling to insert rod (3) as close as possible to alignment and handling rod (4).

As an indication, the height of rings (7) may vary between approximately 15 and 50 mm. It should also be noted that ring (7) may comprise fittings enabling to temporarily hold it at a given height, on the tubes, as long as a pressure force is not exerted thereon.

According to another feature, the end of each tubular element (1) opposite to the end of coupling with the pedicle screw heads has a tapped socket (12) for example screwed on the caps (6). Into this tapped socket (12) is screwed a pusher member (13) arranged to press on the alignment and handling rod (4) to simultaneously cause the displacement of rings (7) and of curved rod (3). The body of pusher member (13) is formed of a threaded rod (13*a*) having a length substantially equal to that of the tubular elements (1). One of the ends of this threaded rod (13*a*) is fitted with a control handle (13*b*) while its other end is fitted with a tip (13*c*). The tip (13*c*) is rotatably assembled, at the end of threaded rod (13*a*) and has a recess (13*d*) complementary to that of the alignment and handling rod (4).

As a result, when threaded rod (13*a*) is screwed into the socket (12), it is vertically lowered into the tubular element (1) along the screwing to press on alignment and handling rod (4) via tip (13*c*), which is not rotated, while remaining indexed with respect to said rod (13*a*).

As a result, a screwing action exerted by the pusher member (13) causes the displacement of tip (13*d*) which presses on rod (4), to ensure, along with the screwing action, the displacement of the different rings (7), the heights of which have been previously adjusted to compensate for dimensional deviations between said rod (4), which is rectilinear, and implantable rod (3), which is curved. The displacement of rings (7), pressing on rod (3), displaces said rod to position it in the corresponding pedicle screws.

Such a positioning is possible given that the screw heads (2) are totally disengaged after the coupling and the alignment of the tubular elements (1), which are performed from the outside of said pedicle screw heads. For example, at the time of the intervention, the pusher members (13) are respectively assembled substantially at the ends and in the middle of the series of considered tubular elements.

It should also be reminded that the end of each considered tubular element (1) opposite to the end cooperating with the pedicle screw heads receives an added collar (8) having a having a laterally protruding part (8a) for the insertion of a rod (5) intended to maintained the adjustment obtained after having removed rod (4).

It should be reminded that the different tubular elements (1) are connected two by two at their free end by a spacer member (9).

The variable positioning of collars (8) enables to adapt the spacer members, for example, to the patient's morphology.

Spacer member (9) has a variable length, to be selected by the surgeon; this length determines the distance between tubular elements, which causes the relative displacement of the vertebrae. This enables the surgeon to control the curvature of the section of the implanted column, and thereby to restore a physiological curvature (for example, thoracic kyphosis).

A range of different lengths is provided for the spacer members.

Each spacer member enables to attach two contiguous tubular elements having a position forming an angle between them. Each spacer member is formed of a plate having two round holes, each provided with a ring forming a mobile pivoting joint, inserted in the thickness of the plate. The holding occurs when the ring is slid along each tubular element.

Each pedicle screw head (2) is formed by a socket having a recess (2a) for the engagement of the implantable curved rod (3). According to the invention, the pedicle screw head (2) is continued on either side of recess (2a), by breakable tabs (2b) and (2c). In the same way as the socket tapping, tabs (2b) and (2c) are threaded for the installation of a nut (10) to fasten the rod (3) in the corresponding pedicle screw head. The nut (10) is installed by an actuation member (11), engaged into the tubular elements (1), after having removed rod (4) and having positioned rod (5) in the collars (8), externally to the tubular elements (1).

Given the features forming the basis of the correction device according to the invention, the method is described hereafter in relation with FIGS. 7 to 19.

Figure 7:
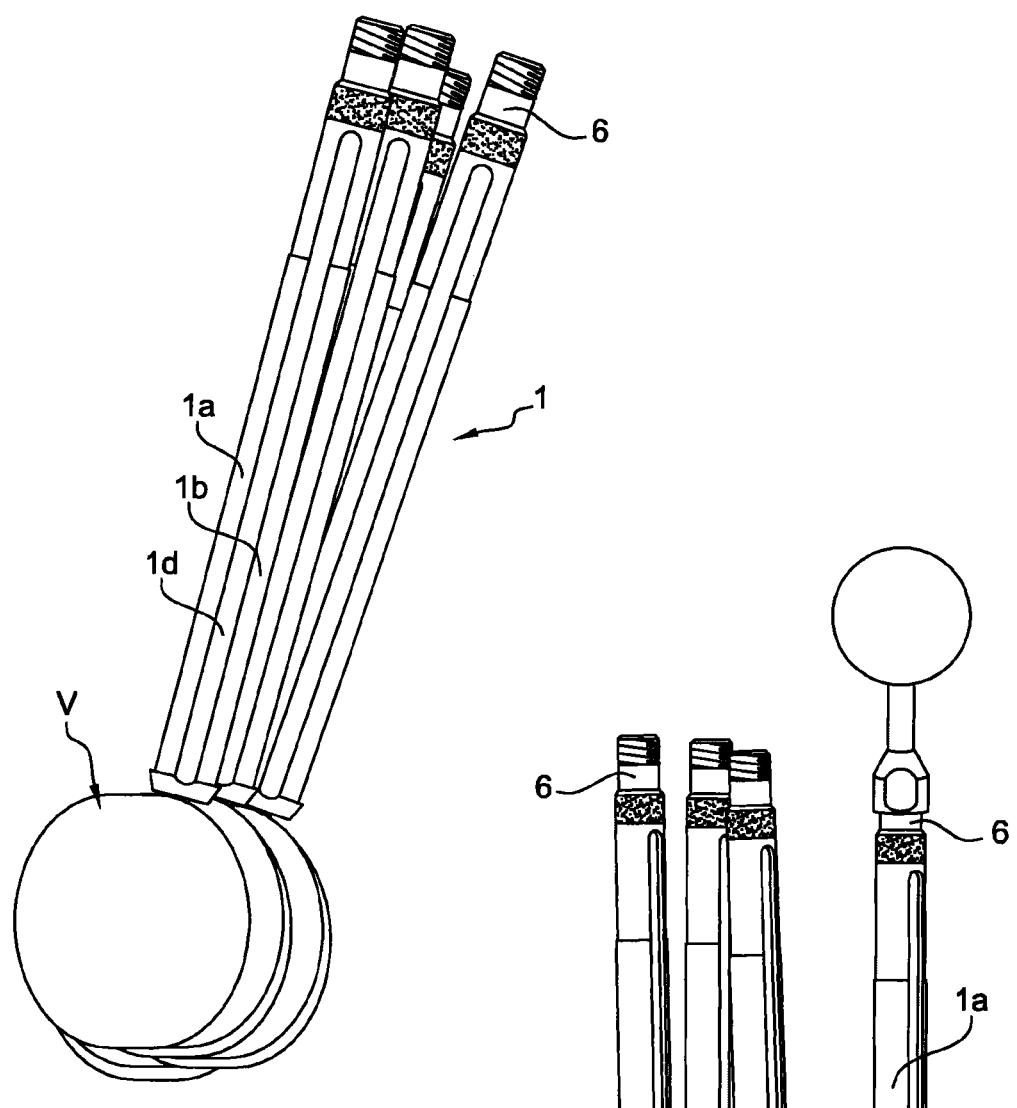
FIGS. 7 to 19 are perspective views showing the main steps of the correction of the spinal column by means of the surgical device according to the invention.

In each of the screw heads (2), tubular elements (1) are coupled in the previously-indicated conditions, that is, on the outside of the screw heads, to clear the inside of said screw heads (FIG. 7).

The different finned pedicle screws (2), fitted with the tubular elements (1), are fastened into the spinal bodies (V) on each side thereof. It should be noted that the pedicle screw heads may be one-piece or polyaxial, as perfectly well known by those skilled in the art.

Figure 8:
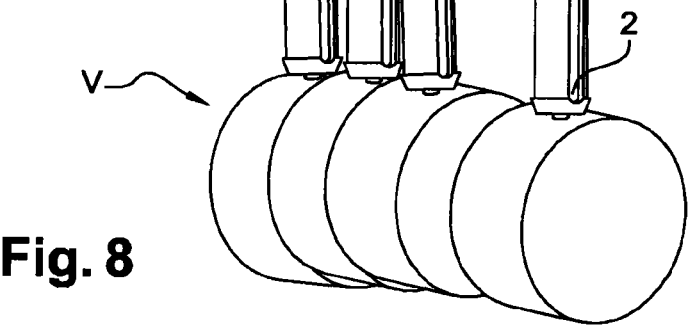

Each tubular element (1) is then equipped with its cap (fastening nut) (6) (FIG. 7). Similarly, it is possible to use a round handle to use the tubular element as a screwdriver; this control handle cooperating with the caps (FIG. 8). The ring (7) is positioned in the upper portion of the considered tubular element. At this stage, the tubular elements (1) are angularly shifted in correspondence with the spine deformation.

Figure 9:
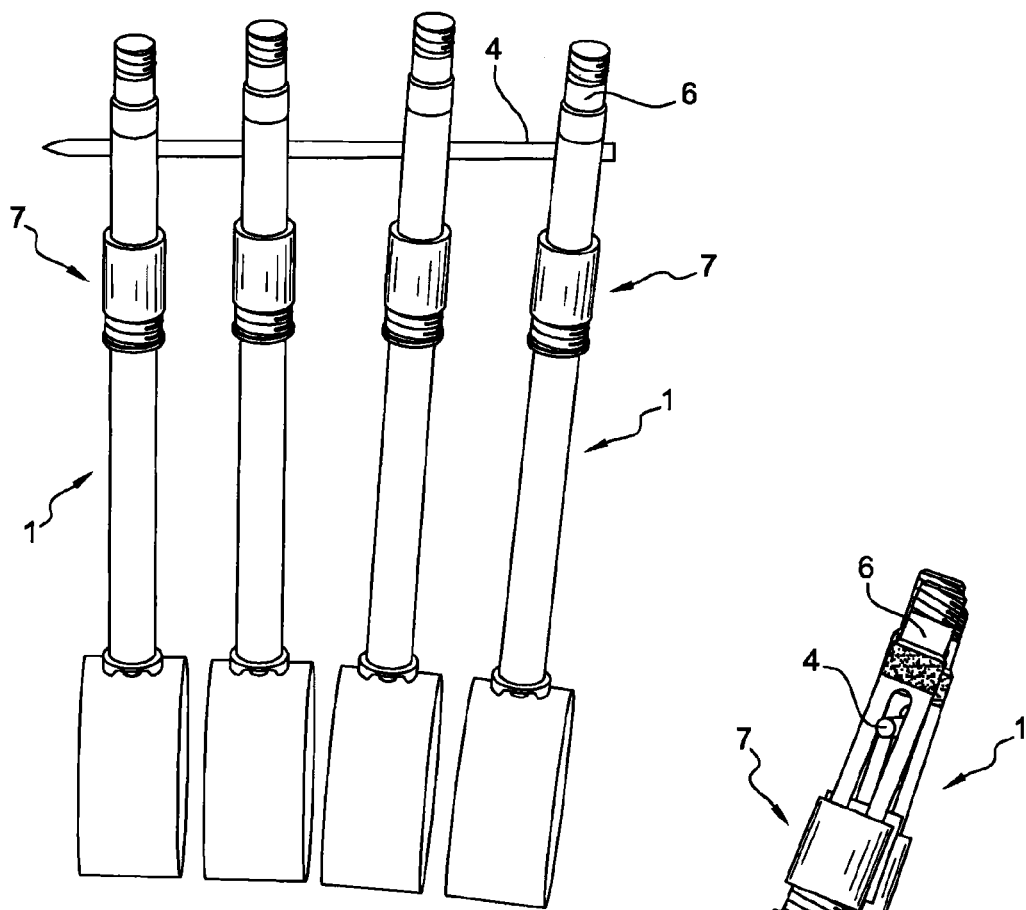
Figure 10:
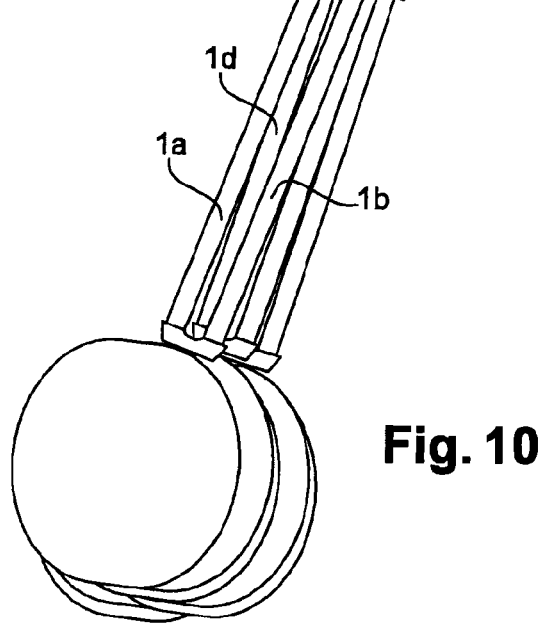

Rod (4) is then engaged through slots (1c) and (1d) of the different tubular elements (1) and above the rings (7) to cause their progressive straightening up in order to align them by simultaneously generating a translation, a tilting, and a rotation of the vertebrae in the three planes of space for the spine correction (FIGS. 9 and 10).

Figure 11:
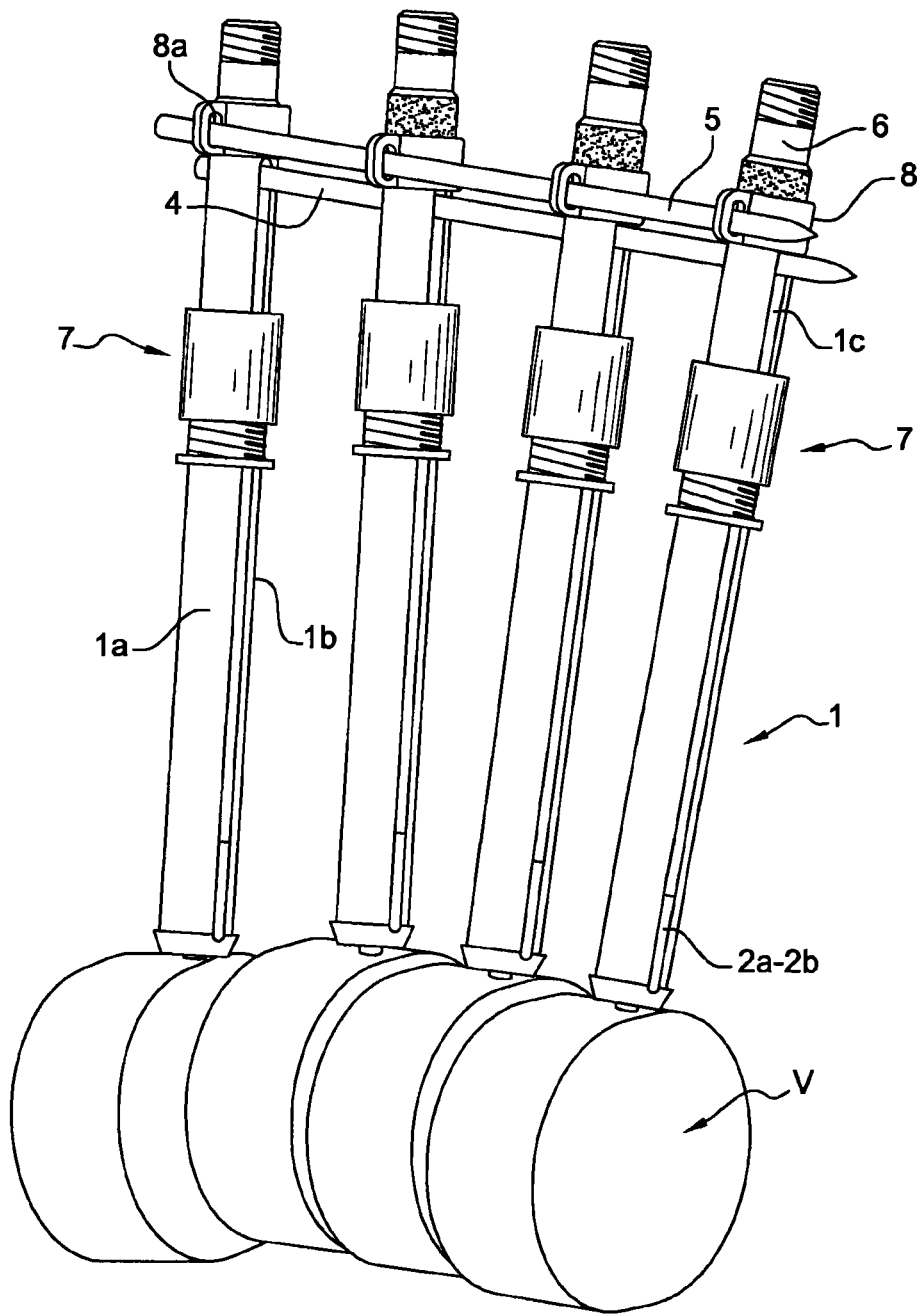
Figure 12:
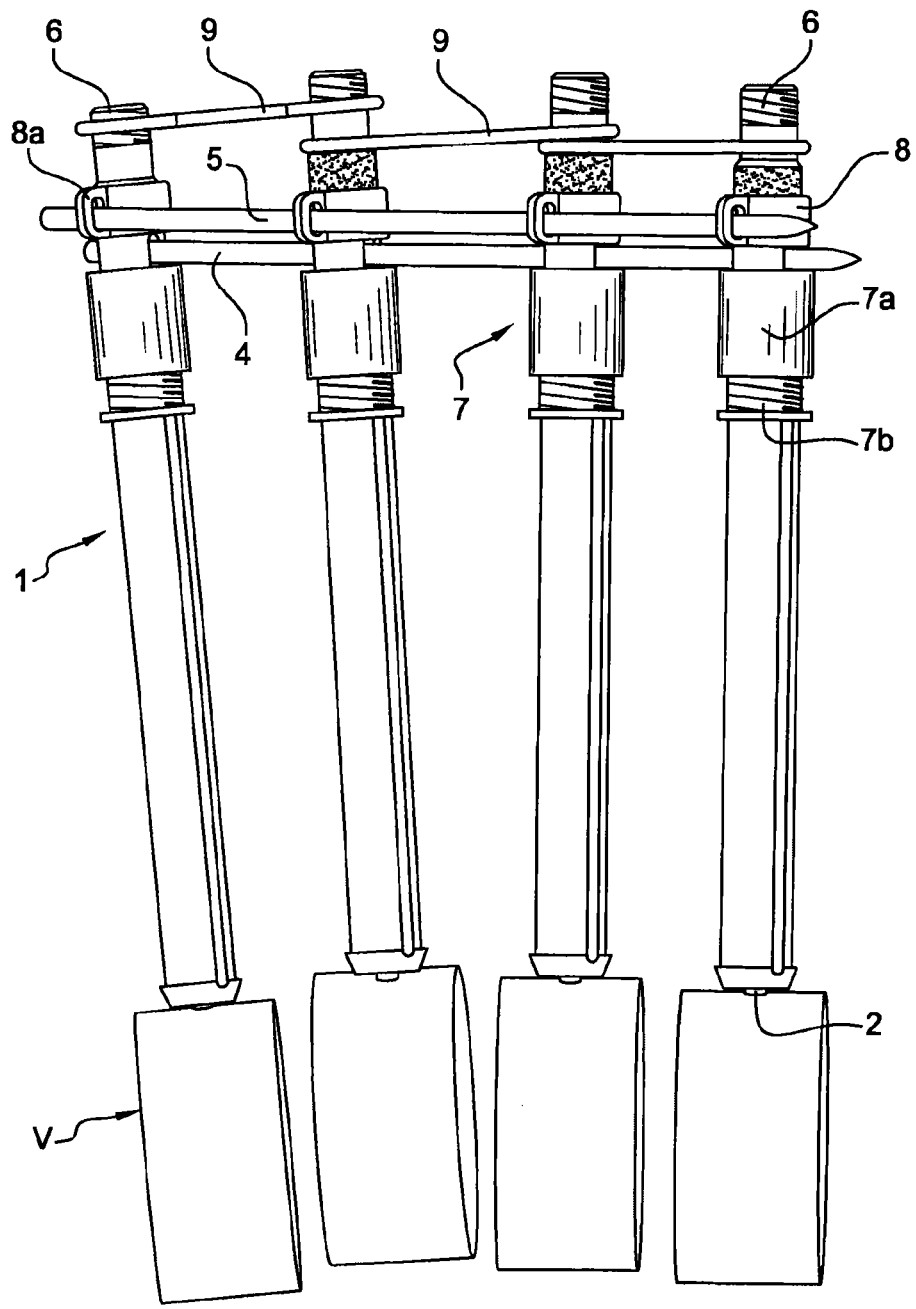
Figure 13:
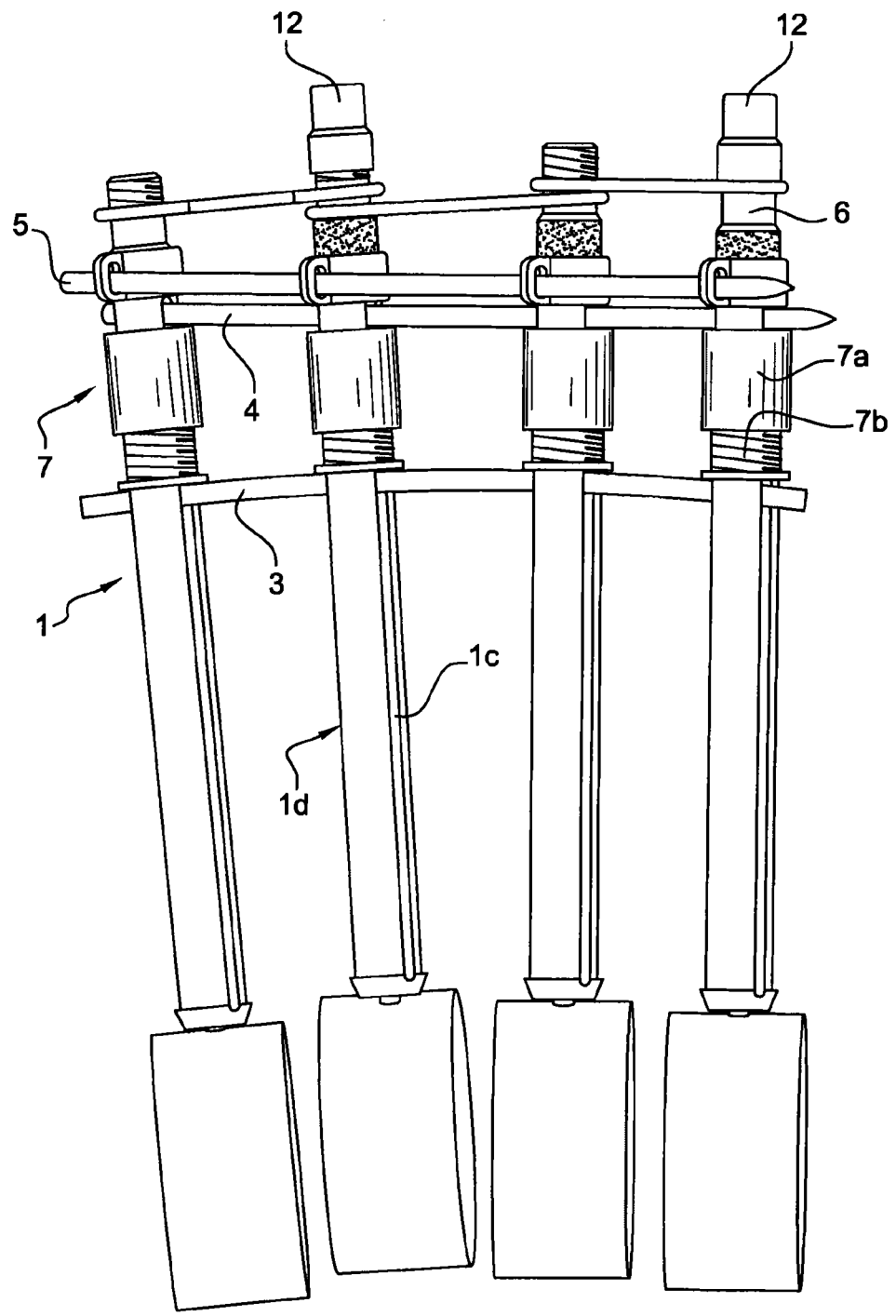

The collars (8) are also arranged in the upper portion of the tubular elements (1) for the insertion of rod (5) (FIG. 11).

The different tubular elements (1) are then coupled two by two by the spacer members (9) (FIG. 12) to predetermine the expected curvature correction, such as a thoracic kyphosis, for example.

Figure 14:
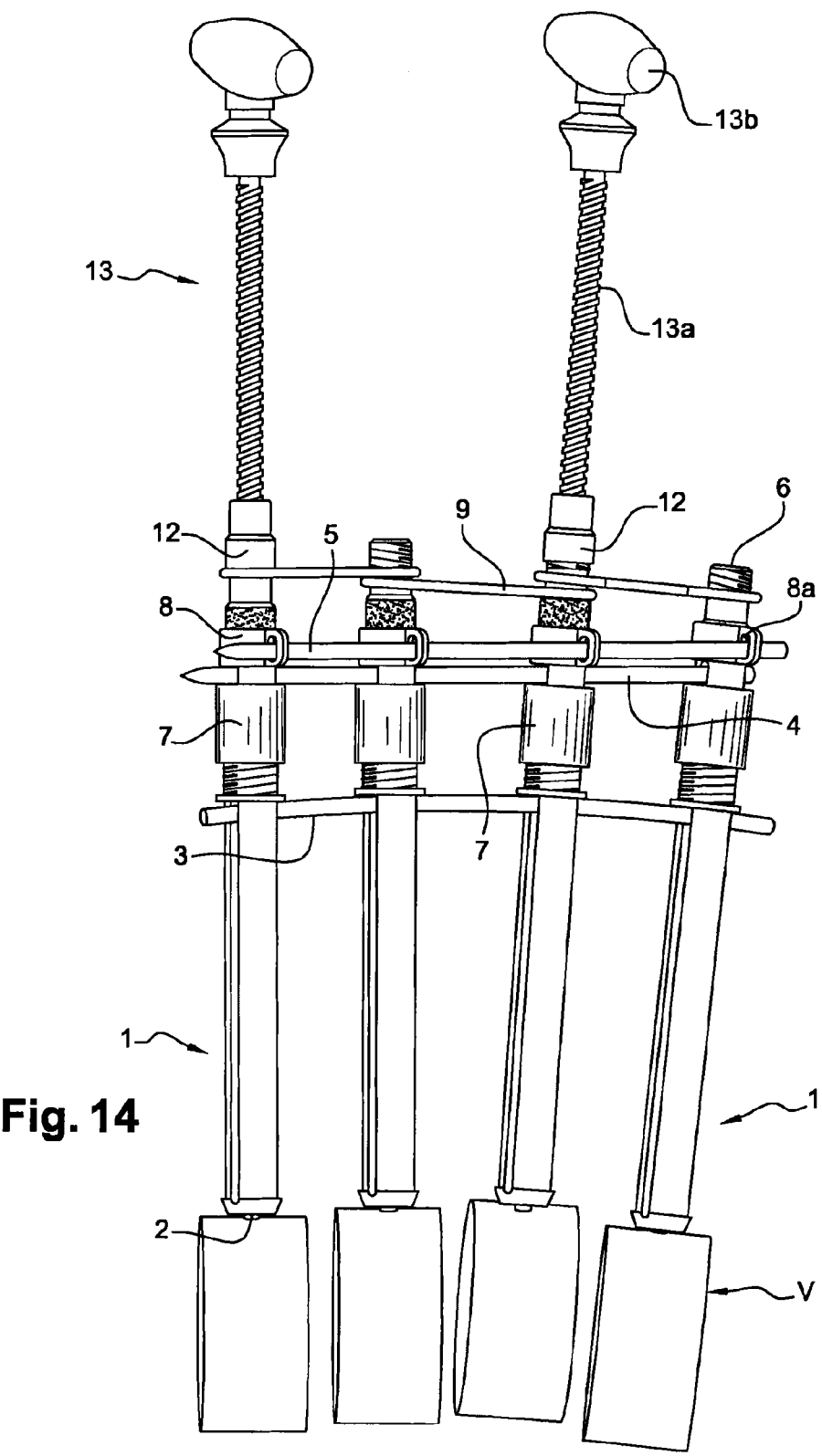
Figure 15:
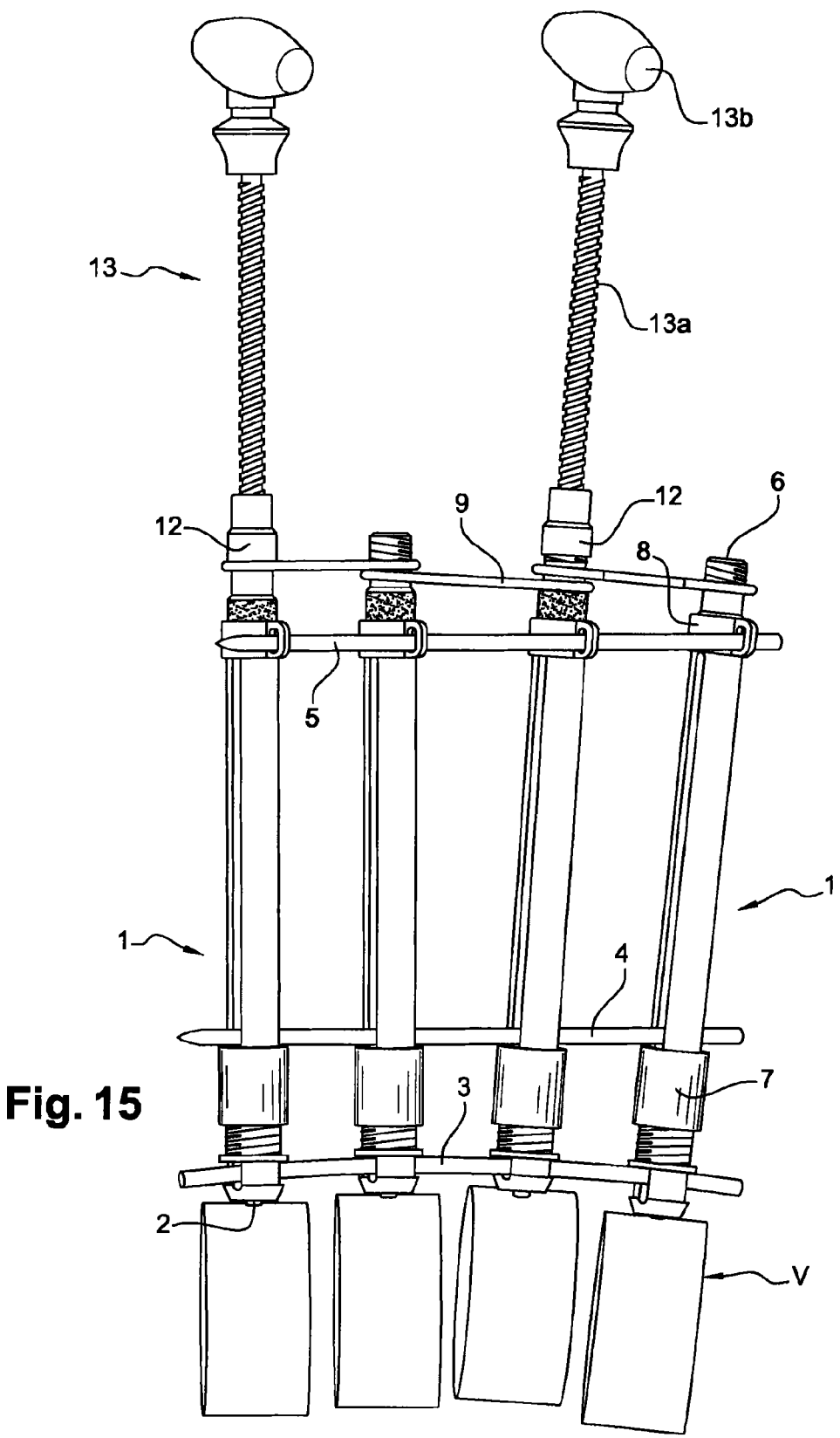

Under rings (7) (FIG. 13), is transversely engaged implantable curved rod (3) for its positioning and fastening in the pedicle screw heads (2a). For this purpose, the free ends of certain tubular elements (1) are fitted with tapped socket (12), for the screwing of the pusher member (13) having its tip (13d) pressing on rod (4) (FIG. 14). The screwing action of the pusher member (13) causes the displacement of the different rings (7) and the simultaneous displacement of curved rod (3) until it positions in the recesses of the sockets of the pedicle screw heads (FIG. 15).

Figure 16:
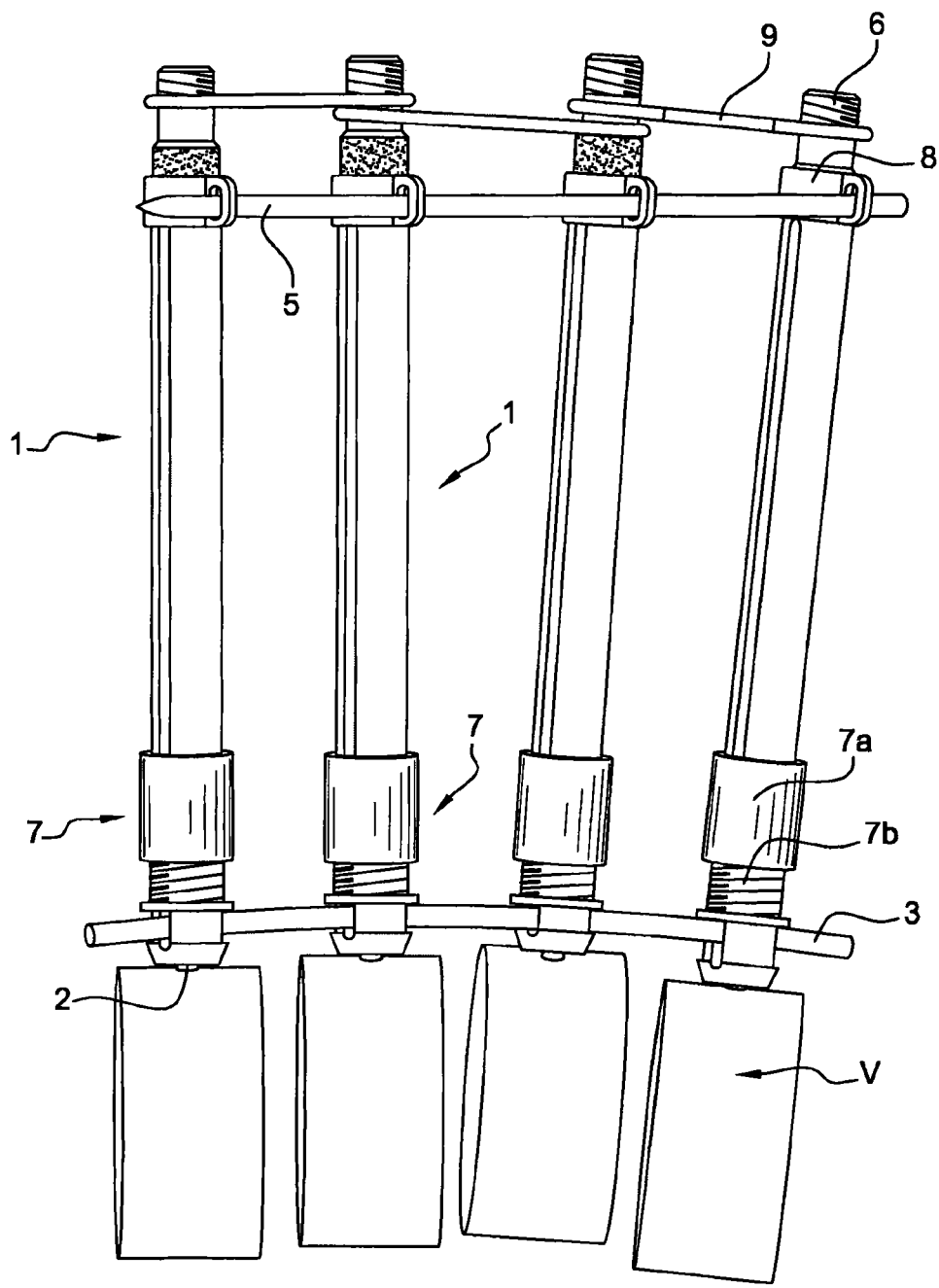
Figure 17:
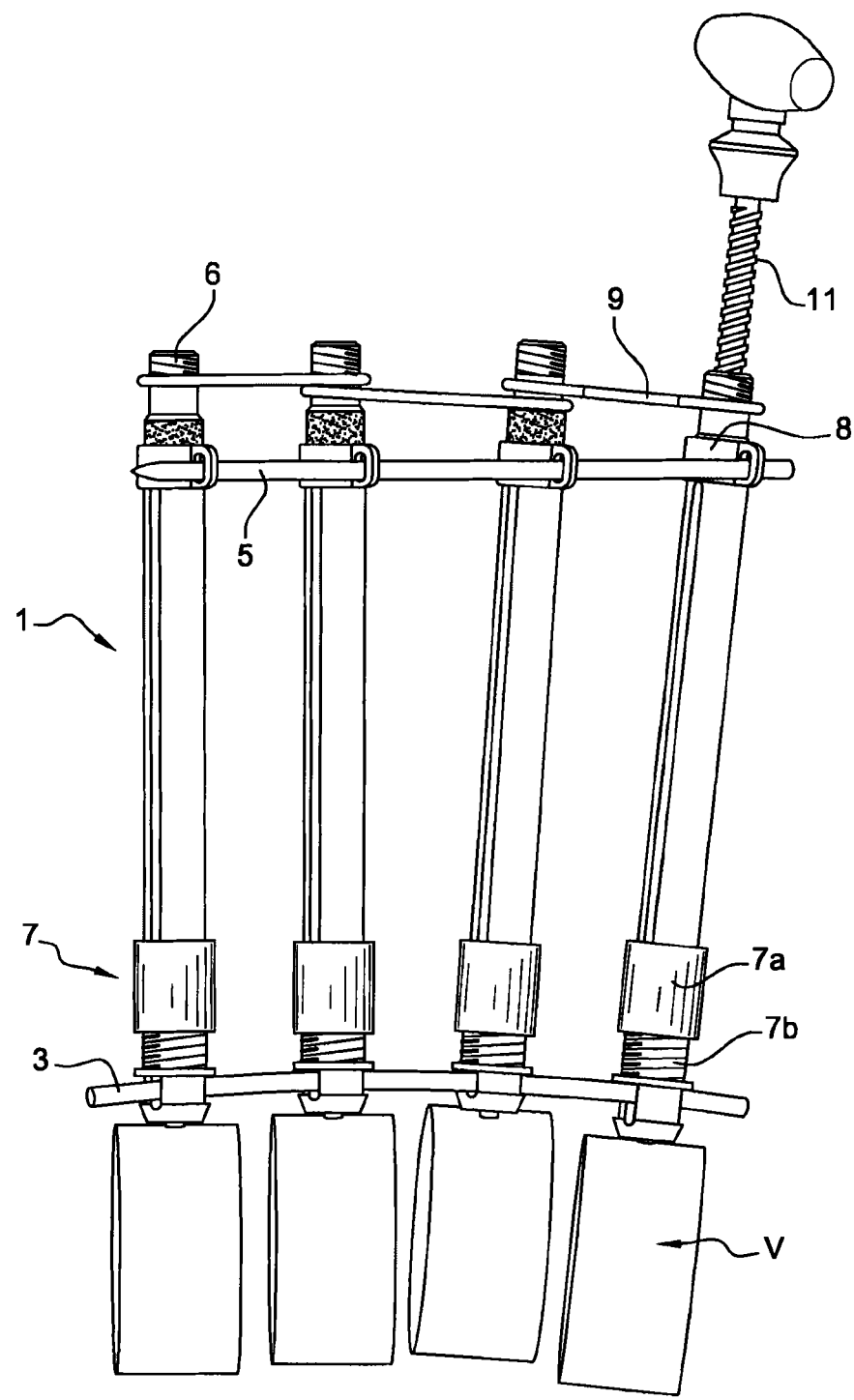

The pusher members (13) and the handling rod (4) are then removed (FIG. 16).

It should be noted that the aligned tubular elements (1) altogether enable, due to a rod of variable selected length, to mobilize a determined group of vertebrae, and to apply thereto a displacement aiming at driving the ribs attached to the vertebrae. This enables to correct deformations of the rib cage forming the gibbosity of scoliotic patients. This mobilization of a limited group of vertebrae and of the ribs which are attached thereto may be performed after having generally reduced in the three planes of space the position of all the vertebrae.

The inside of the different tubular elements (1) and of the pedicle screw heads (2), being totally free, it is accordingly possible to introduce nuts (10) through the different tubular elements (1) by an appropriate actuation member (11) (FIG. 17) and to screw the nuts (10) into the pedicle screw heads to provide the fastening of implantable rod (3).

Figure 18:
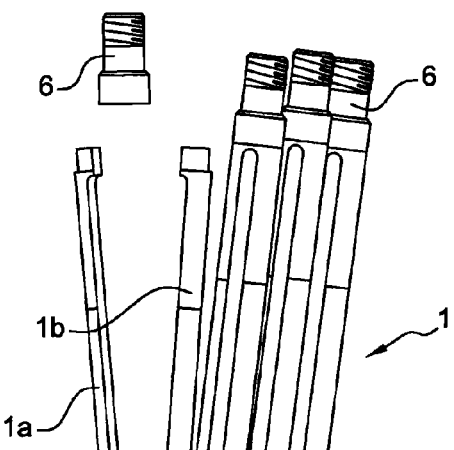

At this stage of the operating mode, it is then possible to take apart the device and, accordingly, to remove the tubular elements (FIG. 18).

Figure 19:
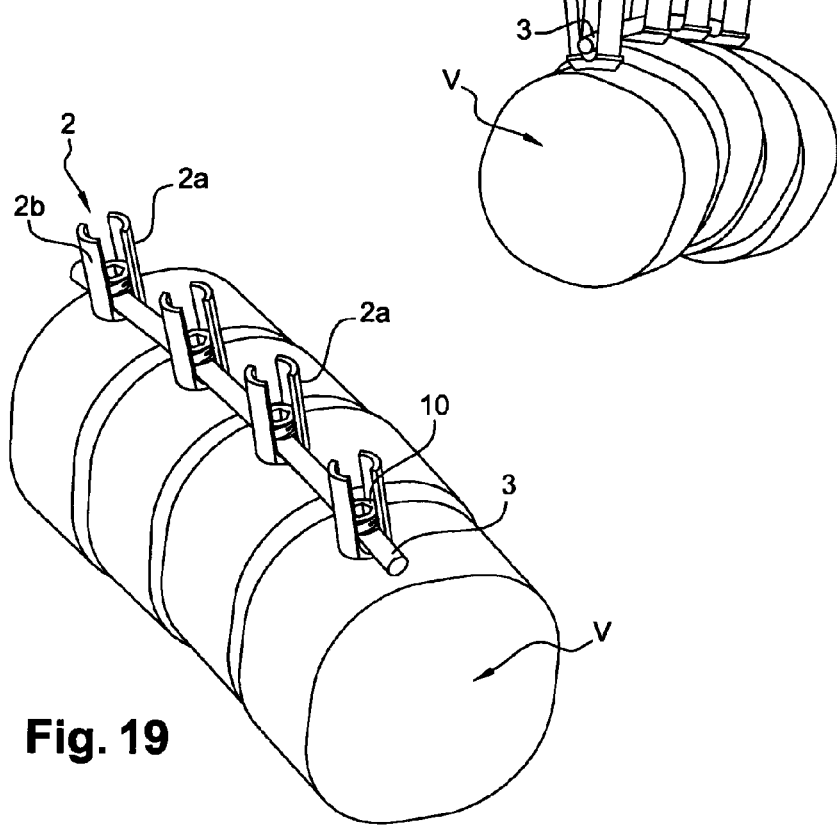

It is then sufficient to fully screw the nuts (10) by means of a member for connecting and definitively fastening the curved rod (3) in pedicle screw heads (2), to break breakable portions (2b) and (2c) of the pedicle screws (2) (FIG. 19).

The advantages well appear from the description and, in particular, those following from document FR 1151331 should be underlined and reminded:

The height adjustment of the bearing rings to compensate for the dimensional deviations corresponding to the lordosiskyphosis profile.

The use of a pusher member to ease the lowering of the implantable rod, with the lowest possible effort.

The invention claimed is:

1. A surgical device for correcting deformations in a spinal column comprising an implantable curved rod, pedicle screw heads arranged to be connected by the curved rod, tubular elements configured for being temporarily attached at a level of the pedicle screw heads, each tubular element being configured to be coupled to an outside of a respective pedicle screw head and having diametrically opposite slots, a first alignment and handling rod configured to be movably inserted into the slots of each tubular element to align the tubular elements for correction of said spinal column by translation, tilting, and rotation of vertebrae in three planes of space, displacement means configured for displacing the curved rod, previously inserted into the slots of each tubular element, towards the pedicle screw heads upon displacement of the first alignment and handling rod within the slots, wherein the displacement means comprise, for each respective tubular element, a ring assembled with the ability to slide along said respective tubular element, wherein each ring is height-adjustable along the respective tubular element to compensate for dimensional deviations between the first alignment and handling rod and the curved rod, and wherein the surgical device further comprises a second alignment and handling rod coupled to the outside of the aligned tubular elements and configured to maintain adjustment of the tubular elements after removal of the first alignment and handling rod from the slots, and a plurality of nuts for fastening the curved rod in the pedicle screw heads wherein the tubular elements are configured to receive, each in turn, an actuation member inserted therein for actuating a nut of said plurality for fastening the curved rod in each of the pedicle screw heads.

2. The surgical device of claim 1, wherein each ring comprises two parts coupled together in height-adjustable fashion.

3. The surgical device of claim 1, in combination with a pusher member, wherein an end of each tubular element, remote from the respective pedicle screw head, comprises a tapped socket for threadably receiving the pusher member, and the pusher member is arranged to press on the first alignment and handling rod to cause displacement of the displacement means and of the curved rod.

4. The surgical device of claim 3, wherein the pusher member comprises a threaded rod configured for being screwed into the tapped socket, one end of said threaded rod being fitted with a control handle, while an other end of said threaded rod is fitted with a rotatably assembled tip having a recess with a section complementary to that of the first alignment and handling rod.

5. The surgical device of claim 1, wherein an end of each tubular element, remote from the respective pedicle screw head, has an added collar with a laterally-protruding portion for insertion of the second alignment and handling rod.

6. The surgical device of claim 1, wherein each tubular element comprises two independent parts, one end of each part having fittings for coupling said parts together and with the respective pedicle screw head.

7. The surgical device of claim 6, wherein the fittings of the coupling comprise two forks connected in jointed fashion, to enable to space apart the parts to position the parts with respect to the respective pedicle screw head, and then to push the parts back.

8. The surgical device of claim 7, wherein an other end of each part cooperates, after having been pushed back, with a hollow connection nut to form the tubular element, said parts delimiting the diametrically opposite slots.

9. The surgical device of claim 1, further comprising a third alignment and handling rod having a variable selected length and connecting a selected group of the tubular elements, said group being selected after correction and alignment in the three planes of space, to ensure a selective mobilization enabling to correct a gibbosity.

* * * * *